(12) United States Patent
Calvert

(10) Patent No.: US 8,967,029 B1
(45) Date of Patent: Mar. 3, 2015

(54) TOXIC MOSQUITO AERIAL RELEASE SYSTEM

(71) Applicant: TMARS Associates, Trustee for Toxic mosquito aerial release system CRT Trust, Manassas, VA (US)

(72) Inventor: S. Mill Calvert, Manassas, VA (US)

(73) Assignee: TMARS Associates, Trustee for Toxic mosquito aerial release system CRT Trust, Manassas, VA (US)

(*) Notice: Subject to any disclaimer, the term of this patent is extended or adjusted under 35 U.S.C. 154(b) by 0 days.

(21) Appl. No.: 14/549,305

(22) Filed: Nov. 20, 2014

(51) Int. Cl.
| | | |
|---|---|---|
| B64D 1/18 | (2006.01) |
| F41H 13/00 | (2006.01) |
| B64D 1/02 | (2006.01) |
| A01K 67/033 | (2006.01) |
| A01K 5/00 | (2006.01) |
| B64C 39/02 | (2006.01) |

(52) U.S. Cl.
CPC ...... *F41H 13/00* (2013.01); *B64D 1/02* (2013.01); *A01K 67/033* (2013.01); *A01K 5/00* (2013.01); *B64C 39/024* (2013.01); *B64C 2201/024* (2013.01); *B64C 2201/128* (2013.01); *B64C 2201/146* (2013.01)
USPC ............... 89/1.11; 244/136; 239/8; 239/171

(58) Field of Classification Search
CPC ........... F41H 13/00; F42B 12/56; B34D 1/02; B34D 1/08; B34D 1/10; B34D 1/12; G05D 2201/02096; B64C 2201/024; B64C 2201/128; B64C 2201/146; B64C 39/024; A01K 5/00; A01K 67/033
USPC ............. 89/1.11, 1.1; 244/136; 119/650, 651; 239/8, 171, 172
See application file for complete search history.

(56) References Cited

U.S. PATENT DOCUMENTS

| | | | | |
|---|---|---|---|---|
| 2,098,887 | A * | 11/1937 | Satterlee ................... | 244/136 |
| 2,730,402 | A * | 1/1956 | Whiting et al. ............ | 239/341 |
| 4,260,108 | A * | 4/1981 | Maedgen, Jr. ............. | 239/171 |
| 4,585,112 | A * | 4/1986 | Peeling et al. ............. | 194/293 |
| 5,148,989 | A * | 9/1992 | Skinner ..................... | 239/171 |
| 5,785,245 | A * | 7/1998 | Tedders et al. ............ | 239/9 |
| 5,794,847 | A * | 8/1998 | Stocker ..................... | 239/8 |
| 6,651,377 | B1 * | 11/2003 | Pleasants .................. | 43/55 |
| 6,799,740 | B2 | 10/2004 | Heller et al. | |
| 7,413,145 | B2 | 8/2008 | Hale et al. | |
| 2014/0246545 | A1 * | 9/2014 | Markov ..................... | 244/190 |

* cited by examiner

*Primary Examiner* — Bret Hayes
(74) *Attorney, Agent, or Firm* — Louis Ventre, Jr.

(57) ABSTRACT

A device for the aerial release of mosquitoes includes an unmanned aerial vehicle operable by remote control. It carries a container holding a central processing unit and a mosquito breeding bin, which is a self-contained volume housing mosquitoes and a mosquito food having a toxin suitable to be transmitted by mosquito bite after the mosquito consumes the mosquito food. A release tube is connected to the mosquito breeding bin and sized to release mosquitoes from the mosquito breeding bin. A valve is connected to the release tube and is operable by remote control so that when opened, the mosquitoes have an open pathway out of the container through the release tube.

3 Claims, 1 Drawing Sheet

TOXIC MOSQUITO AERIAL RELEASE SYSTEM

TECHNICAL FIELD

In the field of aeronautics, disclosed is an aircraft having structure enabling aerial breeding and discharge of mosquitoes.

BACKGROUND ART

Governments have sought after weapons that can be used to deliver chemicals, viral and bacteriological substances for lethal and non-lethal administration to assembled masses of people. Non-lethal uses typically include peacekeeping operations, for use in actions not considered "military operations," and against terrorists or state actors in war. In this sense, such weapons can be used to control both armed enemies and civilians. Not all uses of such weapons are prohibited by treaty. The present invention is capable of delivering lethal and non-lethal toxins, including any agent that can be carried and administered by a mosquito.

In the United States, lethal chemical weapons are regulated by the Convention on the Prohibition of the Development, Production, Stockpiling and Use of Chemical Weapons and on their Destruction, which entered into force in 1997. This treaty is usually referred to as the Chemical Weapons Convention. It is an arms control treaty with 165 signatory countries and it outlaws the production, stockpiling, and use of chemical weapons and their precursors. The treaty has been interpreted to allow the development of non-lethal chemicals, such as calmative and gastrointestinal convulsives, when classified as riot control agents. Additionally, non-lethal weapons involving calmative agents have been studied for use by the U.S. armed forces.

In the United States, lethal biological weapons are regulated by the Convention on the Prohibition of the Development, Production and Stockpiling of Bacteriological (Biological) and Toxin Weapons and on their Destruction (usually referred to as the Biological Weapons Convention. This is a 1972 treaty banning the production of microbial and other biological agents or toxins and their means of delivery. This treaty has been interpreted not to apply to the biological agents or toxins themselves, but rather certain purposes for which they may be employed which are prohibited. Thus, there are permitted purposes defined to include prophylactic, protective and other peaceful purposes. The biological agents or toxins may not be retained in quantities that have no justification or which are inconsistent with the permitted purposes.

In times of armed conflict and the pursuit of destroying an enemy, living organisms and infected materials derived from them have been used by state and non-state actors. For example, in 300 BC, the Greeks polluted the wells and drinking water supplies of their enemies with animal corpses. Other examples abound in history: in 184 BC, Hannibal's army sent snakes to the enemy led by King Eumenes of Perganium and achieved a victory; in 1346, the Tartars catapulted bodies infected with plague into what is now the Ukraine; in the 1500's, Spanish conquistadors killed off the inhabitants of Central and South America with small pox and measles; in the 1700's British forces used blankets contaminated with small pox to infect North American Indians; in the early 1940's the Japanese armed forces dropped bombs containing up to 15 million plague infected fleas on the Chinese cities of Quxian and Ning-hsien; in the 1990's, Aum Shinrikyo in Japan attempted terrorism at least 10 times to use anthrax, botulinum toxin, Q fever agent and Ebola virus in aerosol form; in 1995, Iraq confirmed that it had produced and deployed bombs, rockets and aircraft spray tanks containing *Bacillus anthracis* and botulinum toxin.

Well known methods of a toxin delivery include dispersion effected by using an aerosol spray, explosive, and direct food or water contamination. Aerosol sprays were thought to be the most effective means of widespread dissemination because an infectious material could travel tens of miles in an inhalable particle size. However factors like particle size of the agent, stability of the agent under desiccating conditions and ultraviolet light, wind speed, wind direction, and atmospheric stability are known to alter the effectiveness of a delivery system.

Explosions to accomplish dispersion are likely to inactivate biological agents and therefore are not very effective in disseminating infectious materials. Contamination of water supplies generally requires an addition of an unrealistically large amount of biological agents to a city supply.

Less lethal toxins are sometimes described as neural inhibitors, gastrointestinal convulsives, neuropharmacological agents, calmative agents, and disassociative hallucinogens. Their delivery systems are designed for use against armed enemies, rioters, and groups of potentially hostile civilians. Calmative agents include an array of psychoactive substances that induce sleep or create disabling hallucinations. An example is BZ (3-quinuclidinyl benzilate, a compound related to scopolamine) previously developed during the Cold War.

SUMMARY OF INVENTION

A device for the aerial release of mosquitoes includes an unmanned aerial vehicle operable by remote control. It carries a container holding a central processing unit and a mosquito breeding bin, which is a self-contained volume housing mosquitoes and a mosquito food having a toxin suitable to be transmitted by mosquito bite after the mosquito consumes the mosquito food. A release tube is connected to the mosquito breeding bin and sized to release mosquitoes from the mosquito breeding bin. A valve is connected to the release tube and is operable by remote control so that when opened, the mosquitoes have an open pathway out of the container through the release tube. When the unmanned aerial vehicle has a lifting blade that causes a downdraft, then the release tube is preferably of a length such that the mosquitoes released therefrom avoid the downdraft from the lifting blade. A compressed gas source may be used to encourage the release of the mosquitoes out of the release tube.

Technical Problem

A mosquito delivery system for lethal and non-lethal applications is not available. If such a delivery system enabling legal non-lethal uses were available, it could later be adapted for military uses should legal restraints be altered or eliminated. For example, one unquestionably legal application of the toxic mosquito delivery system is immunization made possible by adding a toxin, that is, a genetically modified bacterium capable of activating a person's immune system to fight malaria, to mosquitoes. Those contaminated mosquitoes could be aerially released to immunize at risk populations against malaria.

Throughout military history, the health of one's troops has always been an important determining factor. Soldiers on the ground can only properly function if they are not ill, sick, or dying from a deadly virus or pathogen. A soldier, whose immune system is trying to fight a bug or pathogen, will have no energy or ability to fight other soldiers. Sickness can be a very valuable military tool that can be more devastating than the most up-to-date military guns and equipment.

Since making the enemy troops sick is an important military objective, one must then look at what means are available to get the pathogens, germs, and viruses to the enemy.

In today's highly-advanced military technology, there are various types of small robotic devices that can try to get sickness agents close to enemy troops. Even with all of the sophisticated computer chips and microprocessors, all of these high-tech devices cannot come close to the miraculous technology of nature. Nature has a very highly technical device that can not only carry a sickness agent to the area where the enemy may be located, but these devices can seek out and find the enemy even if they are behind fortifications and are in hiding.

This miracle of technology can carry a sickness agent, covertly go to the enemy area, specifically find the individual enemy, and can contaminate the enemy with absolutely no warning. This ultra high-tech device of nature is called a mosquito. If only there was a way for military planners to harvest and use the power of the mosquito, they could easily sicken and kill large masses of enemy troops without even a single shot being fired.

Solution to Problem

The answer to aerial delivery of mosquitoes for medical purposes or for integrating military technology together with the power of the mosquito has now been solved with the invention of the toxic mosquito aerial release system. With this new technology, insects can now be more important than individual immunizations or than tanks or laser guided bombs.

The toxic mosquito aerial release system works by having a small RF controlled drone that includes a flying mosquito-breeding laboratory. All of the conditions are perfect for mosquitoes to be born, to eat and become contaminated, and to safely evacuate the toxic mosquito aerial release system when it is flying above the targeted enemy. Swarms of mosquitoes will then fly down and bite the enemy. As the enemy swats at a mosquito that just bit him, he will not realize that this toxic mosquito bite is much more effective than a bullet.

Advantageous Effects of Invention

With the toxic mosquito aerial release system, large masses of people can be immunized or enemy troops can now be wiped out or rendered useless without having to risk or endanger our own troops. The toxic mosquito aerial release system is extremely low cost and can easily accomplish what a billion dollars in medical interventions and air strikes cannot do.

The mosquitoes in the toxic mosquito aerial release system can be contaminated with various types of genetically altered bacteria to activate the immune system, or contaminated with toxic sickness agents depending on the objectives. For military purposes, the mosquitoes may be used to deliver an agent such as malaria to create sickness, or they could use much more toxic or highly contagious agents and viruses. A highly contagious virus could wipe out 100% of the enemy troops because the ones that did not get bitten will be contaminated by their fellow soldiers.

The toxic mosquito aerial release system is a new and needed technology. It is a way to administrative curative or immunological injection, to administer calmative agents, or to administer deadly disease to wipe out and disable the enemy at a minimal cost. For use in conflict, there is no longer the need to spend countless billions of dollars and to destroy entire areas with bombing, and to wound or sacrifice our bravest and finest soldiers. When it comes down to the hell of war or the miraculous, beautiful technology of a mosquito, the choice will be easy to make.

BRIEF DESCRIPTION OF DRAWINGS

The drawings illustrate preferred embodiments of the toxic mosquito aerial release system according to the disclosure. The reference numbers in the drawings are used consistently throughout.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made, without departing from the scope of the present invention.

Figure 1:
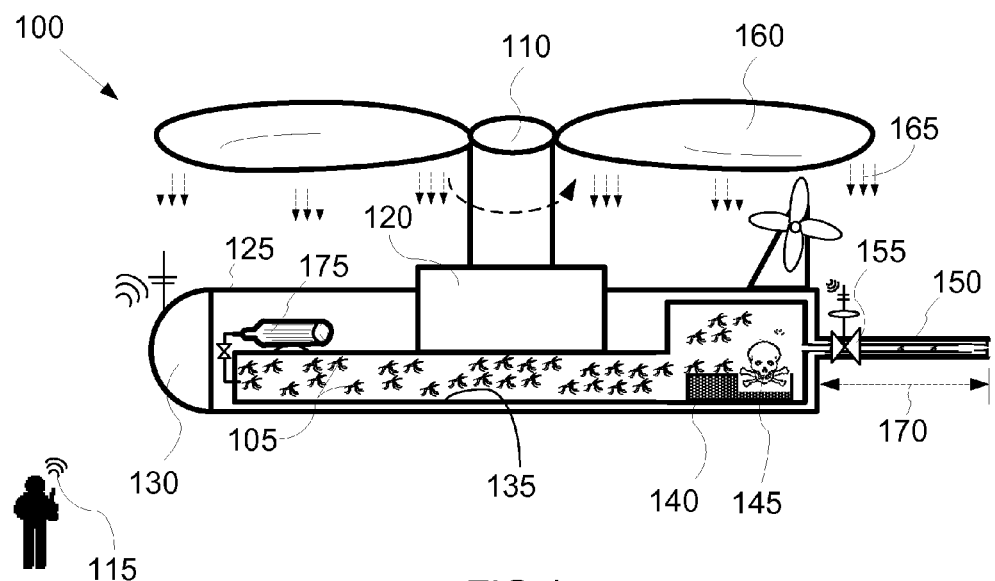
FIG. 1 is a side elevation view of a toxic mosquito aerial release system using a helicopter drone.

FIG. 1 shows a preferred embodiment of a device (100) for the aerial release of mosquitoes (105). It includes: an unmanned aerial vehicle (110); a container (125); a central processing unit (130); a mosquito breeding bin (135); a mosquito food (140); a valve (155); and optionally a compressed gas source (175).

The unmanned aerial vehicle (110) may also be referred to as a drone, a pilotless aircraft, an unpiloted aerial vehicle, an unmanned aerial system; a remotely piloted aircraft, and a growing list of other names well known in the field. The unmanned aerial vehicle (110) includes a motor (120) that, for example, powers a lifting blade (160), that is, it powers one or more lift rotors.

The unmanned aerial vehicle (110) is preferably operable by remote control (115), for example by a pilot on the ground or in another vehicle. The unmanned aerial vehicle (110) may also be autonomously controlled by the central processing unit (130) that is part of the device (100).

The container (125) is connected to, that is attached to, the unmanned aerial vehicle (110) so that the container (125) is carried in the air by the unmanned aerial vehicle (110). The container (125) is the housing that serves as a means for attaching to it or to contain or within it, the central processing unit (130), the mosquito breeding bin (135), the mosquito food (140), any compressed gas source (175), the toxin (145), the release tube (150) and the valve (155).

The central processing unit (130) is held by the container (125). The central processing unit (130) is the hardware within a computer that carries out the instructions of a computer program by performing the basic arithmetical, logical, control and input/output operations of the system. It is the means to automate functions of the device (100) in lifting off and releasing the mosquitoes (105) when conditions warrant or when so instructed by the remote pilot. The central processing unit (130) is either within the container or attached to it. The important criterion is that the central processing unit (130) moves in unison with the unmanned aerial vehicle (110).

The mosquito breeding bin (135) is an enclosed compartment within the container (125). The mosquito breeding bin (135) defines a self-contained volume housing the mosquitoes (105) and allowing them to breed and feed in a confined space.

The mosquito food (140) is housed within the mosquito breeding bin (135), preferably so that it is continuously available to the mosquitoes (105) to consume. Alternatively, the mosquito food (140) may be confined within its own box so that it may be made available to the mosquitoes (105) an appropriate period of time prior to release. Such control can be provided by appropriate operating instructions from the central processing unit (130).

The toxin (145) is within the mosquito food (140). The term "toxin" is used herein to mean any chemical, biological component, bacterium, virus, immunological agent, or other material having an influence on humans and being capable of delivery and transmission to humans via mosquito bite. The toxin (145) must be suitable to be transmitted by mosquito bite after the mosquito consumes the mosquito food (140). An example is genetically modified or weakened malaria parasite altered or combined with hepatitis B virus to trigger an immune response in a human population to protect that population from contracting malaria. Another example is the malaria parasite itself to cause malaria.

The release tube (150) is connected to the mosquito breeding bin (135) so as to provide a pathway for the mosquitoes (105) to exit the mosquito breeding bin (135) into the air outside the container (125). Thus, the release tube (150) is sized to release mosquitoes (105) from the mosquito breeding bin (135).

The valve (155) is connected to the release tube (150) so that it can close off the exit pathway or open it for release of the mosquitoes (105). The valve (155) is controlled by the central processing unit (130) and operable by remote control (115) so that when opened, the mosquitoes (105) have an open pathway out of the container (125) through the release tube (150).

Figure 2:
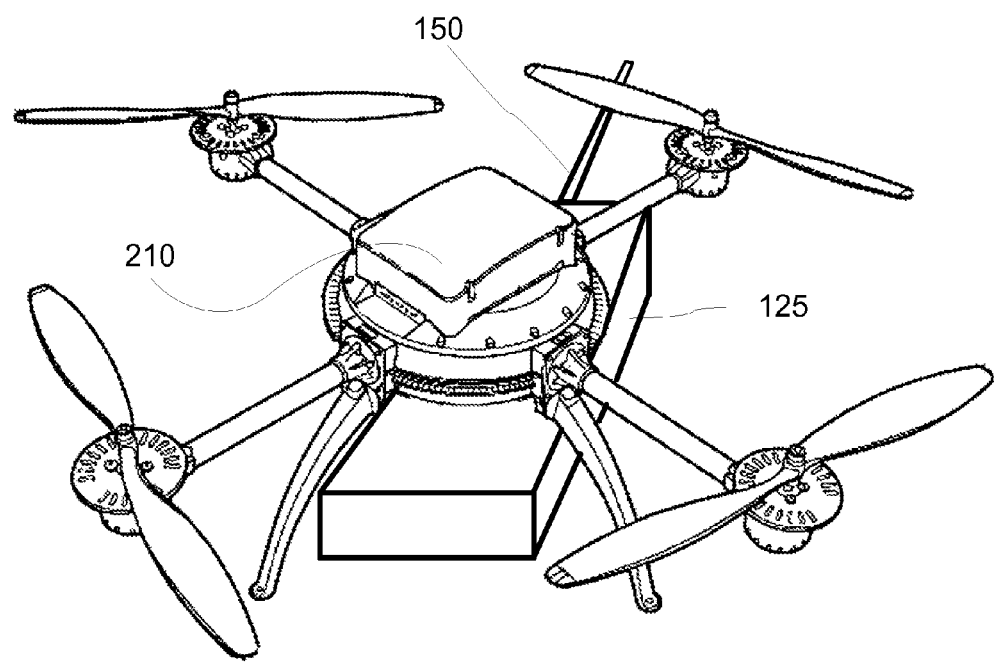
FIG. 2 is a perspective of a second embodiment of the toxic mosquito aerial release system using a four bladed drone.

The unmanned aerial vehicle (110), in one preferred embodiment, includes a lifting blade (160), or propeller, that rotates to cause a downdraft (165) when lifting the device (100) or unmanned aerial vehicle (110). For this embodiment, the release tube (150) has a length (170) such that the mosquitoes (105) released therefrom avoid the downdraft (165) from the lifting blade (160). Other unmanned aerial vehicle embodiments may be used, such as for example, those powered by a turbine, or multiple propellers. One such alternative embodiment, a second unmanned aerial vehicle (210), is shown in FIG. 2 using a multiple propeller lifting means.

The device (100) may include a compressed gas source (175) within the container (125) to add outward flow and encourage the exit of mosquitoes (105) out of the release tube (150). The compressed gas source (175) may be mounted anywhere on the device (100) and will typically be piped to release compressed gas within the mosquito breeding bin (135).

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the aeronautics industry.

What is claimed is:

1. A device for aerial release of mosquitoes comprising:
an unmanned aerial vehicle operable by remote control, the unmanned aerial vehicle comprising a motor;
a container connected to the unmanned aerial vehicle;
a central processing unit held by the container;
a mosquito breeding bin held by the container, the mosquito breeding bin defining a self-contained volume housing mosquitoes;
a mosquito food housed within the mosquito breeding bin;
a toxin within the mosquito food, the toxin suitable to be transmitted by mosquito bite after the mosquito consumes the mosquito food;
a release tube connected to the mosquito breeding bin and sized to release mosquitoes from the mosquito breeding bin; and
a valve connected to the release tube, the valve controlled by the central processing unit and operable by remote control so that when opened, the mosquitoes have an open pathway out of the container through the release tube.

2. The device of claim 1, wherein the unmanned aerial vehicle comprises a lifting blade that rotates to cause a downdraft when lifting the unmanned aerial vehicle; and wherein the release tube has a length such that the mosquitoes released therefrom avoid the downdraft from the lifting blade.

3. The device of claim 1, further comprising a compressed gas source within the container and piped to release compressed gas within the mosquito breeding bin.

* * * * *